United States Patent [19]

Bergman et al.

[11] Patent Number: 4,879,736
[45] Date of Patent: Nov. 7, 1989

[54] X-RAY EXAMINATION APPARATUS

[75] Inventors: Ulf Bergman, Spanga; Jurgen Sommer, Sollentuna; Arne Borggren, Jarfalla, all of Sweden

[73] Assignee: Siemens Aktiengesellschaft, Berlin and Munich, Fed. Rep. of Germany

[21] Appl. No.: 274,275

[22] Filed: Nov. 22, 1988

[51] Int. Cl.$^4$ ............................................. G21K 7/00
[52] U.S. Cl. ..................................... 378/181; 378/167
[58] Field of Search ................ 378/167, 181, 189, 190

[56] References Cited

U.S. PATENT DOCUMENTS 4,412,346 10/1983 Takenouti et al. .................. 378/181
4,761,805 8/1988 Sebring ............................... 378/181

OTHER PUBLICATIONS

"ROTAX II" brochure of BC Medical Manufacturing Co., Ltd., no date.

Primary Examiner—Carolyn E. Fields
Assistant Examiner—David P. Porta
Attorney, Agent, or Firm—Hill, Van Santen, Steadman & Simpson

[57] ABSTRACT

An x-ray examination apparatus has an x-ray image intensifier and an x-ray film changer mounted so that the x-ray film changer can be moved to an exposure position, in front of the x-ray image intensifier, for producing x-ray pictures of an examination subject. The x-ray image intensifier has a holder on which the x-ray film changer is movably mounted so that, when in the exposure position, the film changer has the same image axis as that of the x-ray image intensifier. The film changer is pivotable out of the exposure position by approximately 90° to a standby position. To avoid having the x-ray film changer in the standby position prevent access to a patient on an examination table, and to permit the x-ray image intensifier to be adjusted to any arbitrary position without being impeded by the film changer in the standby position, the examination apparatus has a holder for the film changer in the form of a bearing which at least partially surrounds the x-ray image intensifier. The bearing is disposed in a plane which is substantially perpendicular to the image access, and the film changer is displaceable along the bearing.

8 Claims, 2 Drawing Sheets

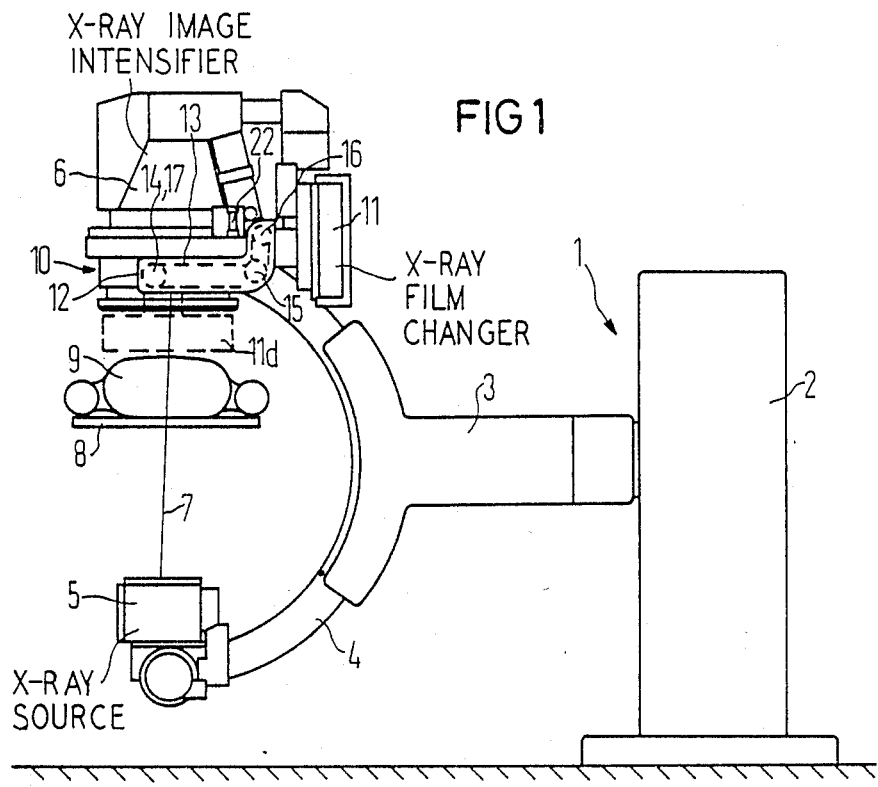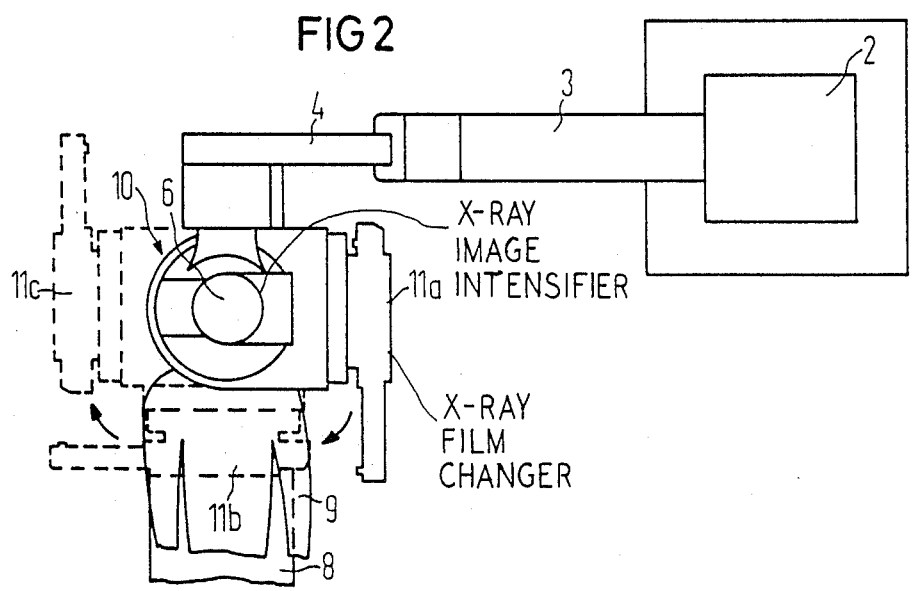

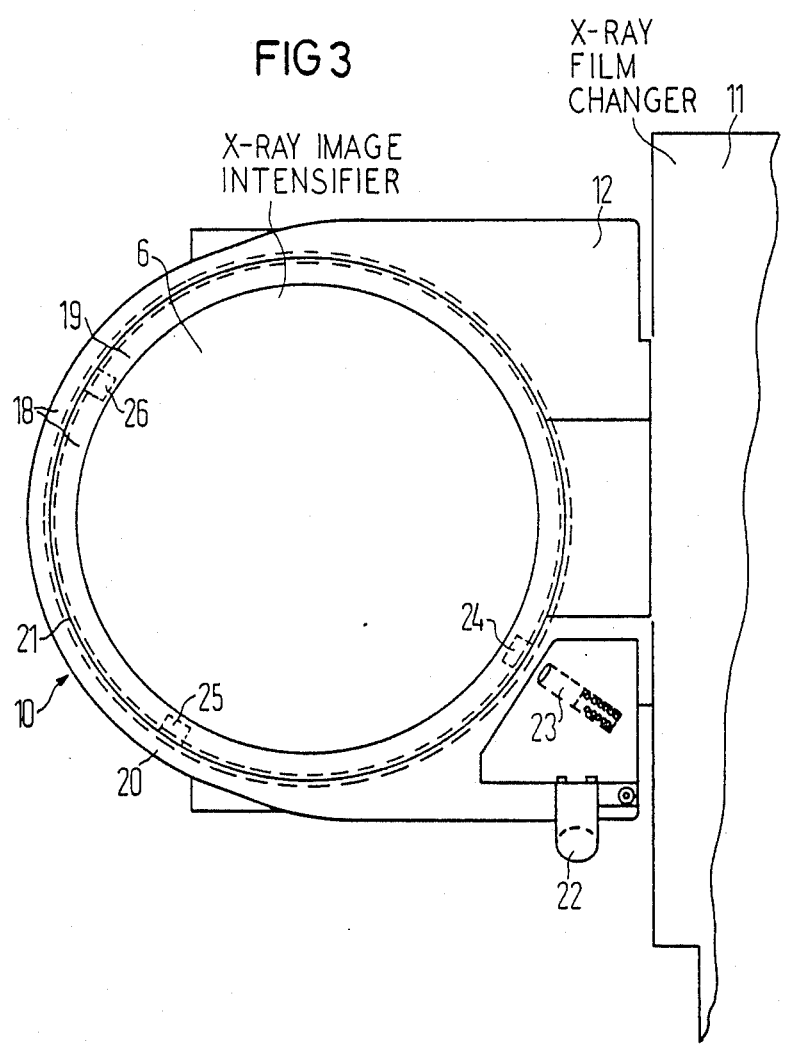

X-RAY EXAMINATION APPARATUS

BACKGROUND OF THE INVENTION

1. Field of the Invention

The present invention is directed to an x-ray examination apparatus, and in particular to such an apparatus having an x-ray image intensifier and an x-ray film changer, with the film changer being mounted so as to be optionally moveable into an exposure position in front of the x-ray image intensifier.

2. Description of the Prior Art

An x-ray examination apparatus having an x-ray image intensifier, with an x-ray film changer mounted so as to be optionally introducible into the beam path in front of the x-ray image intensifier for producing x-ray pictures is commercially available from BC Medical Manufacturing Company Limited, and is described in a brochure from that company. In this commercially available apparatus, the x-ray image intensifier has a holder attached thereto, on which the x-ray film changer is mounted so as to be moveable, with the x-ray film changer in the exposure having the same image access as that of the image intensifier. The film changer can be pivoted out of the exposure position by approximately 90° to a standby position.

The above commercially available installation is suitable, for example, for conducting angiography examinations. In such an examination, the introduction of a catheter into the patient is tracked using the x-ray image intensifier. When a contrast agent is then injected into the patient via the catheter, x-ray exposures are frequently made, for which purpose the x-ray film changer is brought into the exposure position. After the x-ray exposures have been made, the x-ray film changer is again pivoted back to the standby position. In this known x-ray examination apparatus, the holder for the x-ray film changer is rigidly attached to the image intensifier, so that the film changer has only a single standby position. The brochure of BC Medical Manufacturing Company Limited for this apparatus shows one standby position, at which the x-ray film changer lies at the head side, and behind the image intensifier, as seen by a patient lying on an examination table. This standby position of the x-ray film changer is particularly cumbersome for an anesthesiologist because the patient is difficult to reach proceeding from the head side. A further disadvantage of the standby position of the x-ray film changer is that, given a cranial angling of the x-ray image intensifier, the film changer will press against the stomach or chest of the patient, thereby limiting the available angular displacement.

SUMMARY OF THE INVENTION

It is an object of the present invention to provide an x-ray examination installation having an x-ray image intensifier and an x-ray film changer optionally moveable from a standby position to an exposure position in front of the x-ray image intensifier, wherein the film changer in the standby position does not impede access to a patient lying on an examination table, and wherein the x-ray image intensifier can be placed in any arbitrary position relative to the patient without being impeded by the film changer in the standby position.

The above object is achieved in accordance with the principles of the present invention in an x-ray examination installation wherein the holder for the x-ray film changer is a bearing which at least particially surrounds the x-ray image intensifier, the bearing being disposed in a plane substantially perpendicular to the image axis, and the x-ray film changer being displaceable along this bearing. This permits the x-ray film changer, in its standby position, to be displaced dependent on the desired access to the patient, or dependent on the desired angular position of the x-ray image intensifier.

The bearing may be a roller bearing or a smooth bearing. All that is necessary is that the x-ray film changer be easily manually displaceable along the bearing while in its standby position.

In one embodiment of the invention, the holder may be a carriage on which the x-ray film changer is displaceable from the exposure position to the standby position. This permits a simple displacement of the film changer between these positions.

In a preferred embodiment, the carriage is rigidly connected to the bearing, so that the carriage is also shifted given displacement of the x-ray film changer along the bearing. As a result, the x-ray film changer can always be adjusted into the exposure position as needed, independently of its position in the standby position.

Locking means may also be provided along the bearing at selected locations, to lock the film changer at specific locations.

DESCRIPTION OF THE DRAWINGS

FIG. 1 is a side view of an x-ray examination apparatus constructed in accordance with the principles of the present invention.

FIG. 2 is a plan view of the x-ray examination installation shown in FIG. 1.

FIG. 3 is an enlarged plan view showing details of the holder for the x-ray film changer constructed in accordance with principles of the present invention.

DESCRIPTION OF THE PREFERRED EMBODIMENTS

As shown in FIG. 1 an x-ray examination installation constructed in accordance with the principles of the present invention includes a stand 1 consisting of a column or pedestal 2 to which an arm 3 for a C-shaped carrier 4 is attached. An x-ray tube 5 is mounted at one free end of the carrier 4, and an x-ray image intensifier 6 is mounted at the opposite end. The x-ray tube 5 has a central ray 7 centered on the x-ray image intensifier 6. A patient support table 8, on which a patient 9 is disposed, is situated between the x-ray tube 5 and the x-ray image intensifier 6.

The x-ray image intensifier 6 carriers an x-ray film changer 11 via a holder 10. A carriage 12 is connected to the holder 10, which permits the x-ray film changer 11 to be displaced by approximately 90° from an exposure position 11d (shown in dashed lines) to a standby position (shown in solid lines). Such displacement can be undertaken, for example, by drive rollers 14, 15 and 16 entrained by a belt 13, one of the rollers being driven by a motor 17. In the view shown in FIG. 1, the motor 17 is disposed behind the roller 14.

As shown in FIG. 2, the holder 10 surrounds the x-ray image intensifier 6, and permits the x-ray film changer 11 to be displaced to a standby position at any one of locations 11a, 11b or 11c, the latter position being shown in dashed lines. Such movement ensues as indicated by the curved arrows.

As shown in FIG. 3, the holder 10 includes a bearing 18. The inner bearing race 19 in a the form of a ring, is rigidly connected to the x-ray image intensifier 6. The outer bearing race 20, also in the form of a ring, is rotatably seated around the inner race 19. The inner and outer bearing races 19 and 20 are relatively moveable via a bearing medium 21 (schematically indicated by a solid line) which may be, for example, rollers or a slip surface. As can also be seen in FIG. 3, the carriage 12 is integrated with the outer bearing race 20, so that the carriage 12 is also displaced when the film changer 11 is moved around the inner bearing race 20. The x-ray film changer 11 is manually displaceable to various standby positions by a handle 22. A spring-loaded pin 23 is provided for locking the x-ray film changer into anyone of positions 11aa, 11b or 11c shown in FIG. 2. The pin 23 engages one of the recesses 24, 25 or 26 provided in the inner bearing race 19, dependent on the desired position.

If a right brachial catheterization is to be undertaken on the patient 9, the operator swivels the x-ray film changer 11 to the position 11a shown in FIG. 2, so that the pin 23 engages the recess 24. The physician can then conduct the examination without being impeded by the x-ray film changer 11, located at its standby position at the opposite side. For a left brachial catheterization, the x-ray film changer 11 is swiveled to the position 11c shown in FIG. 2, so that the pin 23 engages the recess 26. If it is necessary to have access to the patient from both longitudinal sides of the support table 8 the film changer is brought to the position 11b, so that the pin 23 engages the recess 25.

Given a cranial or caudal rotation of the x-ray image intensifier 6, or of the x-ray source 5, appropriate rotational movements can bring the x-ray film changer 11 to a standby position at which it does not impede the range of motion of the image intensifier 6.

Although modifications and changes may be suggested by those skilled in the art, it is the intention of the inventors to embody within the patent warranted hereon all changes and modifications as reasonable and properly come within the scope of their contribution to the art.

We claim:

1. An x-ray examination installation for examining a patient comprising: means for generating an x-ray beam in which
    said patient is disposed, and having a central ray;
    an x-ray image intensifier having an image axis substantially coincident with said central ray;
    an x-ray film changer;
    means for mounting said x-ray film changer so that said x-ray film changer can be optionally moved through about 90° between an exposure position in front of said x-ray image intensifier and a standby position out of said x-ray beam; and
    bearing means at least partially surrounding said x-ray image intensifier in a plane substantially perpendicular to said image axis, said x-ray film changer being attached to said bearing means and displaceable along said bearing means.

2. An x-ray examination installation as claimed in claim 1, wherein said bearing means is a roller bearing.

3. An x-ray examination installation as claimed in claim 1, wherein said bearing means is a smooth bearing.

4. An x-ray examination installation as claimed in claim 1, wherein said bearing means includes a carriage to which said x-ray film changer is attached.

5. An x-ray examination installation as claimed in claim 4, wherein said carriage is rigidly attached to said bearing means so that said carriage and said x-ray film changer are co-displaceable along said bearing means.

6. An x-ray examination installation as claimed in claim 1, further comprising means for locking said x-ray film changer at selected locations along said bearing means.

7. An x-ray examination installation as claimed in claim 1, further comprising:
    a curved carrier having opposite free ends, said x-ray image intensifier being mounted at one free end of said carrier and said means for generating an x-ray beam mounted at the opposite end of said carrier, with said patient disposed therebetween.

8. An x-ray examination installation comprising:
    means for generating an x-ray beam in which a patient is disposed, and having a central ray;
    an x-ray image intensifier disposed to receive said x-ray beam after attenuation by said patient, said x-ray image intensifier having an image axis;
    an x-ray film changer;
    means for optionally moving said x-ray film changer through 90° between an exposure position in said x-ray beam and a standby position out of said x-ray beam; and
    a carriage connecting said x-ray film changer and said x-ray image intensifier, said carriage having a circular bearing with an inner bearing race at least partially surrounding, and attached to, said x-ray image intensifier, and an outer bearing race rigidly connected through said carriage to said x-ray film changer, said bearing disposed in a plane substantially perpendicular to said image axis and permitting displacement of said x-ray film changer in said plane along said bearing.

* * * * *